US009624157B2

(12) United States Patent
Liang

(10) Patent No.: US 9,624,157 B2
(45) Date of Patent: Apr. 18, 2017

(54) PROCESS FOR THE PREPARATION OF INGENOL-3-ANGELATE FROM 20-DEOXY-INGENOL

(71) Applicant: LEO Laboratories Limited, Ballerup (DK)

(72) Inventor: Xifu Liang, Ballerup (DK)

(73) Assignee: LEO Laboratories Limited, Dublin (IE)

( * ) Notice: Subject to any disclaimer, the term of this patent is extended or adjusted under 35 U.S.C. 154(b) by 0 days.

(21) Appl. No.: 14/415,544

(22) PCT Filed: Jul. 11, 2013

(86) PCT No.: PCT/EP2013/064643
§ 371 (c)(1),
(2) Date: Jun. 10, 2015

(87) PCT Pub. No.: WO2014/012836
PCT Pub. Date: Jan. 23, 2014

(65) Prior Publication Data
US 2015/0329463 A1 Nov. 19, 2015

Related U.S. Application Data

(60) Provisional application No. 61/672,282, filed on Jul. 16, 2012.

(51) Int. Cl.
C07C 69/52 (2006.01)
C07C 67/297 (2006.01)
C07C 67/08 (2006.01)
C07C 67/00 (2006.01)
C07C 67/29 (2006.01)

(52) U.S. Cl.
CPC ............ *C07C 67/297* (2013.01); *C07C 67/00* (2013.01); *C07C 67/08* (2013.01); *C07C 67/29* (2013.01); *C07C 2103/98* (2013.01)

(58) Field of Classification Search
CPC ....... C07C 69/533; C07C 67/00; C07C 67/29; C07C 2103/98; C07C 67/08; C07C 67/297
See application file for complete search history.

(56) References Cited

U.S. PATENT DOCUMENTS 7,449,492 B2    11/2008   Aylward et al.

FOREIGN PATENT DOCUMENTS

| JP | 2008127287 | | 6/2008 |
| WO | WO2005/048954 | * | 6/2005 |
| WO | WO-2012/010172 A1 | | 1/2012 |
| WO | WO2012010172 | * | 1/2012 |
| WO | WO 2012010172 | | 1/2012 |

OTHER PUBLICATIONS

Nickel et al. (Total Synthesis of Ingenol, J. Am. Chem. Soc., 126, 16300-16301, 2004).*
Nickel et al. (Total Synthesis of Ingenol, J. Am. Chem. Soc., 126, 16300-16301, 2004, Supplemental Information 1: Experimental Procedures and Tabular Characterization Data).*
FDA (Picato, Jan. 25, 2012).*
Jakupovic et al. (Diterpenes from Eurhorbia Segetalis, Photochemistry, vol. 47. No. 8, pp. 1583-1600, 1998).*
Appendino, et al., Eur. J. Org. Chem., *Synthesis of Modified Ingenol Esters*, 12:3413-3420 (1999).
Ball, B. et al., *Total synthesis of thapsigargin, a potent SERCA pump inhibitor*, Org. Lett., 9(4):663-666 (2007).
Beeby, P., *Angeloyl chloride: synthesis and utilisation in the partial synthesis of lantadene A (rehmannic acid)*, Tetrahedron Lett., 38:3379-3382 (1977).
Bohlmann, F. et. al., *Struktur and Synthese eines aus Bellis perennis L. isolierten Diesters*, Chem. Ber., 103:561-563 (1970).
Chen, Y. et al. *Total Synthesis of (-)-Baimuxifuranic Acid+*, J. Chem. Research (S) 472-473 (1997).
Hartmann, B. et al., *Improved preparation of angelate esters*, Tetrahedron Lett., 32(38):5077-5080 (1991).
Hiranuma, S. et al., *Regio- and Stereoselective Hydroxylation of Grindelic Acid and Its 3a—Hydroxy Derivative*, Chem Pharm. Bull., 39(8):2167-2169 (1991).
Hohmann et al, *Diterpenoids from Euphorbia peplus*. Planta Med., 66:291-294 (2000).
Hoskins, W.M., *Pyrrolizidine alkaloid analogues. Preparation of semi-synthetic esters of retronecine*, J. Chem. Soc. Perkin Trans. 1:538-544 (1977).
Koot, et al., *Chemistry of insect antifeedants from Azadirachta Indica (part 18): Demethylation and methylation of the C-8 position of the decalin portion of azadirachtin*, Tetrahedron, 51(7):2077-2090 (1995).
Li, et al. *A General Approach from Eudesmane to Isodaucane Sesquiterpenes: Synthesis of 7-Epi-14-isocyano-isodauc-5-ene from alpha-(-)-Santonin*, Synthesis 1:41-44 (2003).
Nagaoka, et al., *Total synthesis of upial*, Tetrahedron Lett., 34:1501-1504 (1993).
Opferkuch et.al., *On the Chemistry of Ingenol, I Ingenol and Some of its Derivatives*, Z. Naturforschung, 36b:878-887 (1981) [With English Abstract].
Sayed et al., *Constituents of Egyptian Euphorbiaceae. IX. Irritant and cytotoxic ingenane esters from Euphorbia paralias L*, Experienta, 36:1206-1207 (1980).
Sorg, B et al., Zur Chemie des Ingenols II [1] Ester des ingenols and des $\Delta^{7,8}$-Isoingenols, Zeitschrift für Naturforschung, 37b:748-756 (Jan. 1, 1982).
Teng, et al., *Regioselective acylation of 3-0-angeloylingenol by Candida Antarctica Lipase B*, Fitoterapia, 80:233-236 (2009).
Uemura et al., *Isolation and structures of 20-deoxyingenol new diterpene, derivatives and ingenol derivative obtained from "kansui"*, Tetrahedron Lett.,15(29):2527-2528 (1974).
Urabe, et al., *An efficient total synthesis of optically active tetrodotoxin from levoglucosenone*, Chem. Asian. J., 1(1-2):125-135 (2006).
Vlad, et al., *Enantioselective synthesis of 11-homodrim-7-en-9a,12,13-triol*, Chem. Nat. Comp., 47(4):574-578 (2011).
Yun, et al., *Stereoelectronic effect for the selectivity in C-H insertion of alkylidene carbenes and its application to the synthesis of platensimycin*, J. Am. Chem. Soc., 131(24):8413-8415 (2009).
A. Nickel et al.; "Total Synthesis of Ingenol"; Journal of the American Chemical Society, vol. 126., No. 50; Dec. 1, 2004; pp. 16300-16301.
International Search Report for PCT/EP2013/064643 dated Aug. 8, 2013.

* cited by examiner

*Primary Examiner* — Yevegeny Valenrod
*Assistant Examiner* — Blaine G Doletski
(74) *Attorney, Agent, or Firm* — Fish & Richardson P.C.

(57) ABSTRACT

The present invention provides a method for preparing ingenol-3-angelate.

7 Claims, No Drawings

PROCESS FOR THE PREPARATION OF INGENOL-3-ANGELATE FROM 20-DEOXY-INGENOL

The invention provides a method for preparing ingenol-3-angelate (PEP005) from 20-deoxy-ingenol by selective oxidation.

BACKGROUND OF THE INVENTION

The compound ingenol-3-angelate (PEP005) [Sayed, M.D. et.al.; Experienta, (1980), 36, 1206-1207] can be isolated from various *Euphorbia* species, and particularly from *Euphorbia peplus* [Hohmann, J, et. al; Planta Med., (2000), 66, 291-294] and *Euphorbia drummondii* by extraction followed by chromatography as described in U.S. Pat. No. 7,449,492. Ingenol has previously been used as a starting point for the semi-synthetic preparation of ingenol-3-esters [Sorg, B. et. al, Z. Naturforschung, (1982), 37B, 748-756] and ingenol-3-ester derivatives [Appendino et. al., Eur. J. Org. Chem. (1999), 3413; Opferkuch et.al., Z. Naturforschung, (1981), 36B, 878], However, the preparation of ingenol-3-angelate and ingenol-3-angelate derivatives from ingenol has not been described. PCT/DK2011/000081 describes the method of preparing ingenol-3-angelate from ingenol by reacting one or both hydroxyl groups in positions 5 and 20 of ingenol with suitable hydroxyl protecting agents followed by esterifying the hydroxyl group at the 3-position and finally removing the hydroxyl protecting groups to obtain ingenol-3-angelate. The present invention discloses a method for obtaining ingenol-3-angelate from 20-deoxy-ingenol derivatives extractable from *Euphorbia* plants.

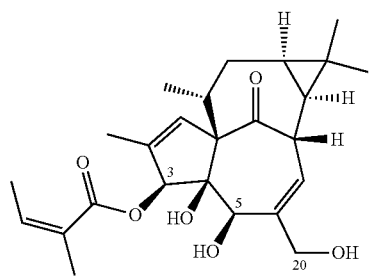

Ingenol-3-angelate

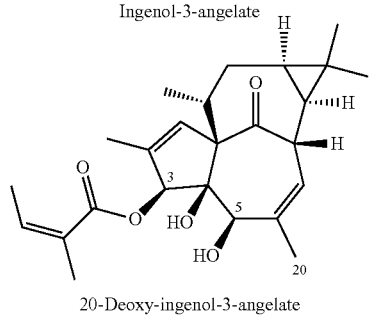

20-Deoxy-ingenol-3-angelate

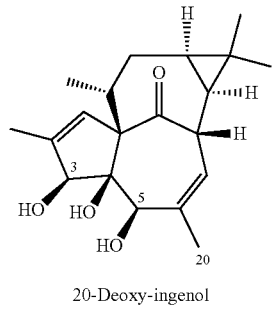

20-Deoxy-ingenol

SUMMARY OF THE INVENTION

The invention provides a method for producing ingenol-3-angelate materials available for example by extraction from plants, The compounds 20-deoxy-ingenol-3-angelate and 20-deoxy-ingenol are both available by extraction of plants and the preparation of ingenol-3-angelate from these starting materials are described, by applying oxidation or oxidation/substitution and optionally angeloylation depending on the starting material. Thus an aspect the invention provides a method for preparing ingenol-3-angelate from 20-deoxy-ingenol by a selective angeloylation to 20-deoxy-ingenol-3-angelate, followed by oxidation to ingenol-3-angelate. If the available 20-deoxy-ingenol-3-angelate is used as starting material, the angeloylation step can be spared and one selective oxidation will provide ingenol-3-angelate, Alternatively, a 20-acyl-ingenol derivative can be generated from as well 20-deoxy-ingenol as from 20-deoxy-ingenol-3-angelate, which can be selectively removed to the desired ingenol-3-angelate.

DETAILED DESCRIPTION OF THE INVENTION

The preparation of angelate esters is not straightforward as angelic acid and angelate esters are prone to isomerisation to form the thermodynamically more stable tiglate esters, both in the presence and absence of base [Beeby, P., Tetrahedron Lett. (1977), 38, 3379-3382, Hoskins, W. M., J. Chem. Soc. Perkin Trans. 1, (1977), 538-544, Bohlmann, F.

et. al, Chem. Ber. (1970), 103, 561-563]. Furthermore, ingenol derivatives are known to degrade in the presence of acid [Appendino et. al. Eur. J. Org. Chem. (1999), 3413]. We have previously described preparation of angelate esters. The 3-angelate ester can be prepared for example by reacting 20-deoxy-ingenol with angeloyl chloride or with angelic acid anhydride in a suitable solvent such as THF and dichloromethane optionally in the presence of a suitable base such as alkali (K, Na, Cs) carbonate, alkali (Li, Na, K) hexamethyl disilazane or N,N-diisopropylethylamine, or by reacting 20-deoxy-ingenol with an acyl donor such angelic anhydride or vinyl angelate optionally in the presence of an enzyme as catalyst.

For example compound II can be synthesised by reacting 20-deoxy-ingenol with an activated angelic acid derivative such as angeloyl halide such as angeloyl chloride. The esterification by reaction with angeloyl chloride can take place without an activator, or it can take place in the presence of a base such as triethylamine, alkali (Li, Na, K, Cs) carbonate or alkali (Li, Na, K) hexamethyldisilazane. Examples of the synthesis of angelic acid esters using angeloyl chloride can for example be found in Beeby, P. J., Tetrahedron Lett., (1977), 38, 3379-3382.

Alternatively, Compound II can for example be synthesised by reacting 20-deoxy-ingenol with an activated angelic acid derivative such as angelic anhydride. The esterification by reaction with angelic anhydride can take place without a catalyst, or in the presence of an acidic catalyst using a Brønsted acid such as perchloric acid or a Lewis acid such as scandium (III) triflate or bismuth (III) triflate, or in the presence of a base such as alkali (Na, K, Cs) carbonate, or alkali (Li, Na, K) hexamethyldisilazane. Examples of the synthesis of angelic acid esters using angelic acid anhydride can for example be found in Hartmann, B. et al, Tetrahedron Lett., (1991), 32, 5077-5080, in JP2008127287 or in PCT/DK2011/000081.

Or compound II can for example be synthesised by reacting 20-deoxy-ingenal with an activated angelic acid derivative such as a mixed anhydride such as angeloyl 2,4,6-trichlorobenzoyl anhydride. The esterification by reaction with a mixed anhydride can take place with a base or in the presence of a base such as sodium hydrogencarbonate or triethylamine, or in the absence of a base. Examples of the synthesis of angelic acid esters using angeloyl-2,4,6-trichloroberizoyl anhydride can for example be found in WO2012 0101072 or Hartmann, B. et al. Tetrahedron Lett. (1991), 32, 5077-5080, or in Ball, B. et al., Org. Lett., (2007), 9, 663-666.

Compound II can for example be synthesised by reacting compound (III), (IV) or (II) with an angeloyl donor such as angelic acid anhydride, angelic acid ester such as vinyl angelate, or angelic acid thioester in the presence of an enzyme such as a lipase or an esterase. Examples of esterification of an ingenol derivative catalysed by lipase can be found in Teng, R. W., Fitoterapia, (2009), 80, 233-236 which is hereby incorporated by reference.

Compound II is then subjected to oxidation by using oxidation agents such as $SeO_2$, bis-(4-methoxyphenyl) selenoxide. In an embodiment $SeO_2$, $SeO_2/SiO_2$, $SeO_2$/cert-butyl peroxide, or $SeO_2$/bis-(4-methoxyphenyl)selenoxide is used. In an embodiment the oxidation is performed in 1,4-dioxane, formic acid/dioxane, MeOH, $AcOH/CH_2Cl_2$, or 1,2-dichloroethane.

In an alternative embodiment the reaction further comprises the steps of reducing 20-aldehyde derivatives to ingenol-3-angelate. In an embodiment the reducing agent is $NaBH_4/CeCl_3$.

In an alternative embodiment the oxidation step is performed in the presence of an acid, and is followed by a de-acylation step.

In an embodiment the starting compound is 20-deoxy-ingenol and the acid ($R'CO_2H$) is formic acid or acetic acid. In an embodiment, the starting material is 20-deoxy-ingenol-3-angelate and the acid can be chosen from almost any available acid, which is compatible with the other reagents. For example the R group can be as well aliphatic saturated and unsaturated, and aromatic of almost any size with due care to solubility etc. In an embodiment deacylation is performed in the presence of an acid or a base in alcohol or by enzymatic transesterification.

In an alternative embodiment the steps comprise bromination with NBS or $Br_2$ followed by a substitution of bromide with an acyloxy group and subsequently by a removal of 20-O-acyl group.

Still for example general formula IV can be prepared by oxidation of 20-deoxy-ingenol to ingenol 20-acylate (VI) in the presence of $SeO_2$/acylic acid followed by 3-O-angeloylation of ingenol 20-acylate (VI). The acyl group can be removed selectively thereby providing the final compound ingenol-3-angelate.

20-deoxy-ingenol used as starting material in the present invention can be isolated from *Euphorbia Kansui* (Uemura et al, Tetrahedron Lett. (1974),15, 2527) or from other *Euphorbia* plants, for example from *Euphorbia Peplus*. Alternatively, the starting material can be 20-deoxy-ingenol-3-angelate, which is also available from plants.

Scheme 1

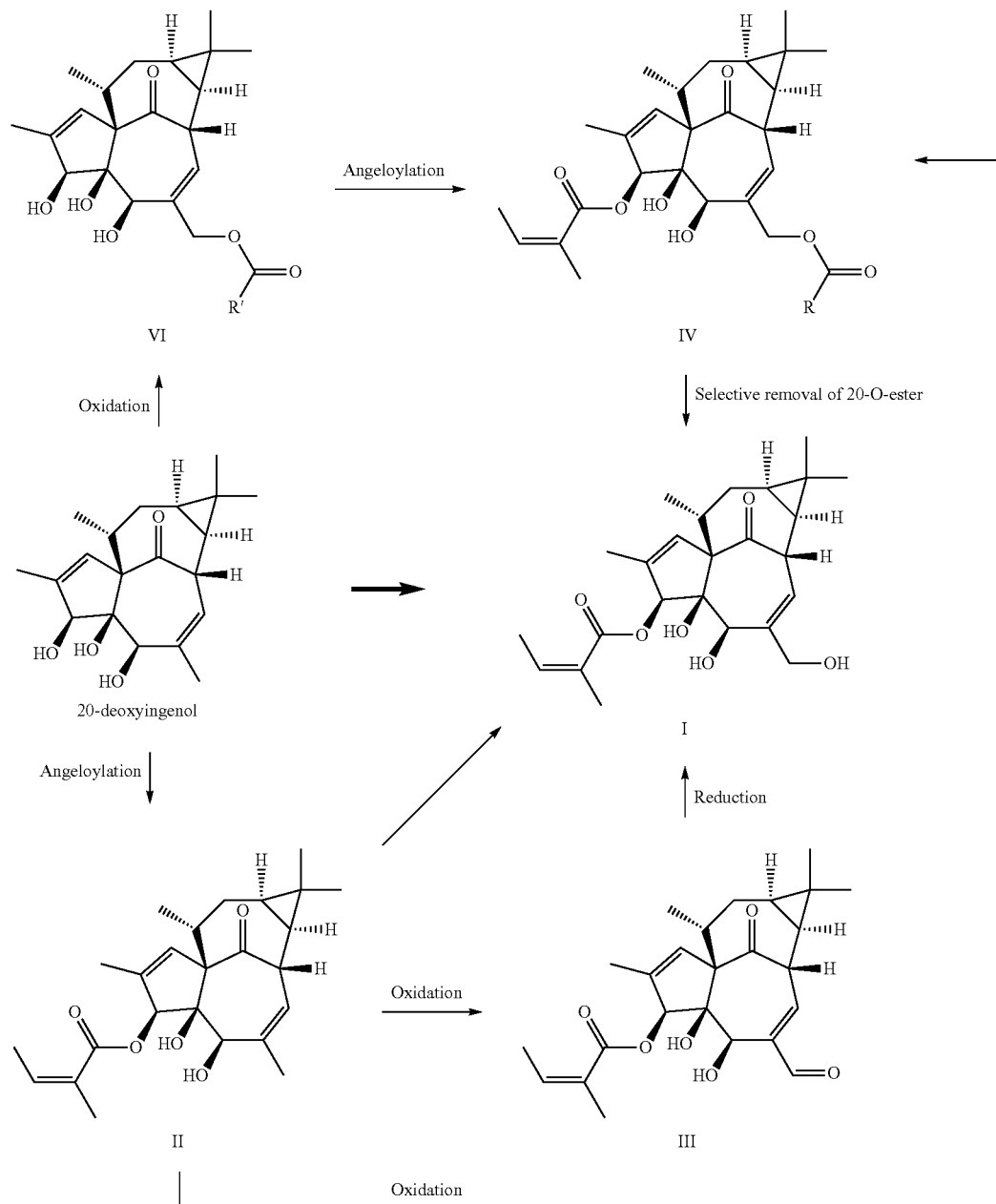

In the first step, angelic acid chloride, angelic mixed anhydride, and angelic anhydride can be used to make 20-deoxyingenol-3-angelate, Both chemical and enzymatic transformations are suitable for this. For the second step, several oxidation reagents such as SeO$_2$, PCC (pyriddinium chlorochromate), and cytochromes can be used. By carefully controlling reaction conditions, we have made ingenol-3-angelate in a small scale. The reaction shows high regioselectivity and proceeds with minimal byproduct formation.

In the oxidation step, if it were not stopped at stage of alcohol, aldehyde would be obtained. The aldehyde can be easily reduced to the alcohol, giving ingenol-3-angelate, The above outline of experiments shows that it is possible to prepare ingenol-3-angelate from 20-deoxyingenol in two steps. If the starting material is chosen to be 20-deoxyingenol-3-angelate, which can be isolated from the *Euphorbia* plant, it is just one step synthesis.

Synthetic Methods

Ingenol-3-angelate (I) of the invention may for example be prepared according to the following non-limiting general methods.

Method A

Ingenol-3-angelate (I) can for example be synthesized by reacting 20-deoxyingenol-3-angelate (II) with a suitable reagent such as selenium dioxide (SeO$_2$), SeO$_2$/SiO$_2$, SeO$_2$/tert-butyl peroxide, and SeO$_2$/bis-(4-methoxyphenyl)selenoxide in a suitable solvent such as 1,4-dioxane, MeOH, AcOH/CH$_2$Cl$_2$, 1,2-dichloroethane. Example of 20-hydroxylation of 20-deoxyingenol can be found in Nickel, A. et al. J. Am. Chem. Soc. (2004), 126, 16300-16301. Examples of allylic hydroxylations of other substrates than I by using those reagents can for example be found in Koot, W.-J., Ley, S. V. Tetrahedron (1995), 51, 2077-2090; Yun, S.-Y. et al. *J. Am. Chem. Soc.* (2009), 131, 8413-8415 or Chen, Y. et al. J. Chem. Research (S) (1997), 472-473.

example be found in Urabe D, et al. Chem. Asian. J. (2006), 125-135; Li, D. R. et al. Synthesis (2003), 41-44.

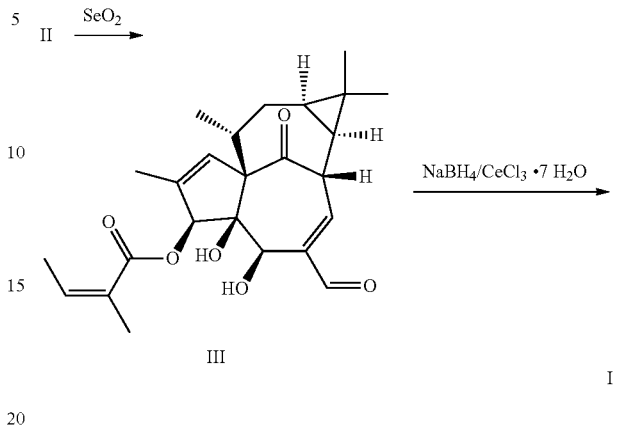

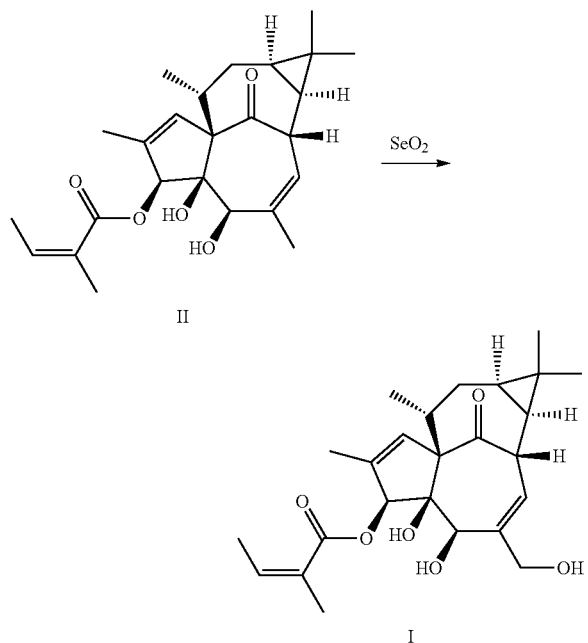

Method B

Ingenol-3-angelate (I) can for example be synthesized by two step reactions. 20-Deoxyingenol-3-angelate (II) can for example be converted to compound III in the presence of a suitable reagent such as SeO$_2$/pyridine and SeO$_2$/tert-butyl peroxide, Compound III can for example be reduced by using NaBH$_4$/Ce$_3$Cl$_3$.7H$_2$O in MeOH, giving I. Examples of allylic hydroxylations of other substrates than I can for Method C Ingenol-3-angelate (I) can for example be synthesized by two step reactions. 20-Deoxyingenol-3-angelate (II) can for example be converted to general formula IV in the presence of SeO$_2$/HCO$_2$H. General formula IV can for example be converted to I by using an acid or base in MeOH, or by enzymatic transesterification, Example of allylic hydroxylation of another substrate can for example be found in Nagaoka, H. et al. Tetrahedron Lett. (1993), 34, 1501-4504. For enzymatic transesterification, see our provisional patent for enzymatic preparation of ingenol-3-angelate US 61/590, 544. Alternatively, general formula IV can for example be synthesized in two steps starting from 20-deoxyingenol, 20-Deoxy-ingenol can for example be oxidized to general formula VI. VI can be converted to IV by selective 3-O-angeloylation.

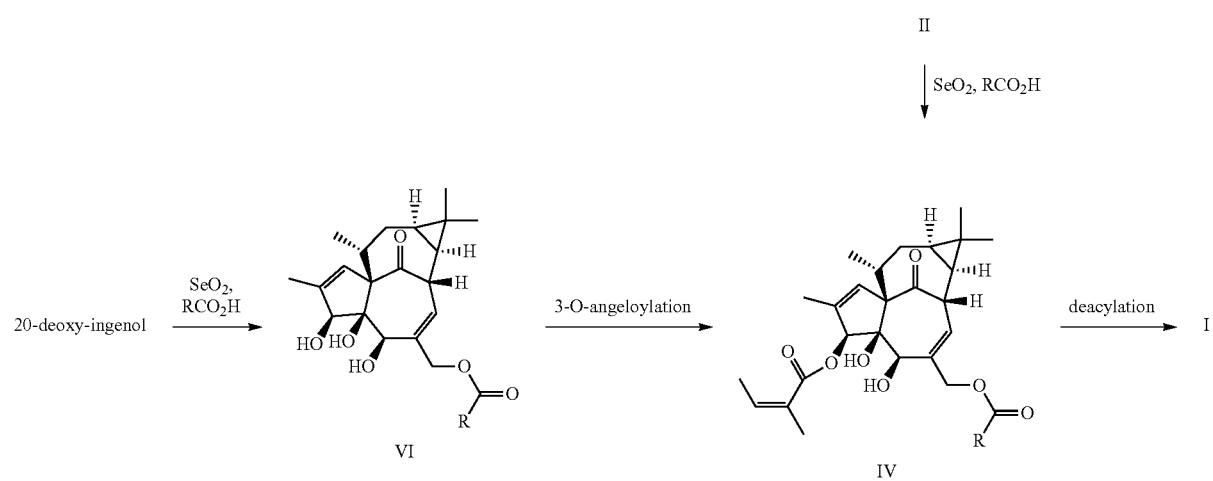

Method D

Ingenol-3-angelate (I) can for example be synthesized by three step reactions. 20-Deoxy-ingenol-3-angelate (II) can for example be reacted with a suitable reagent such as bromine or CUBS, producing V. Compound V can be converted general formula IV. IV can further be converted to I as in method c. Examples of allylic hydroxylations of other substrates than I can for example be found in Hiranuma, S. et al. Chem Pharm. Bull. (1991), 39, 2167-2169; Wad, P. F. et al. Chem. Nat. Comp. (2011), 47, 574-578.

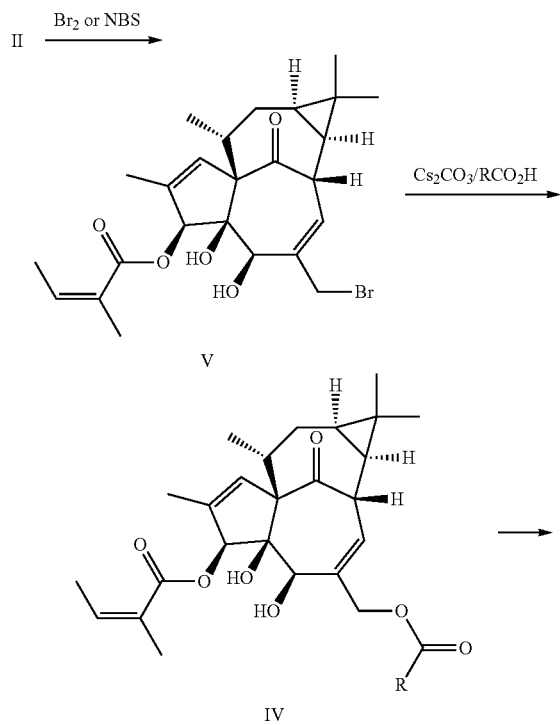

Preparation of Ingenol-3-Angelate (PEP005) from 20-Deoxyingenol-3-Angelate

Example 1

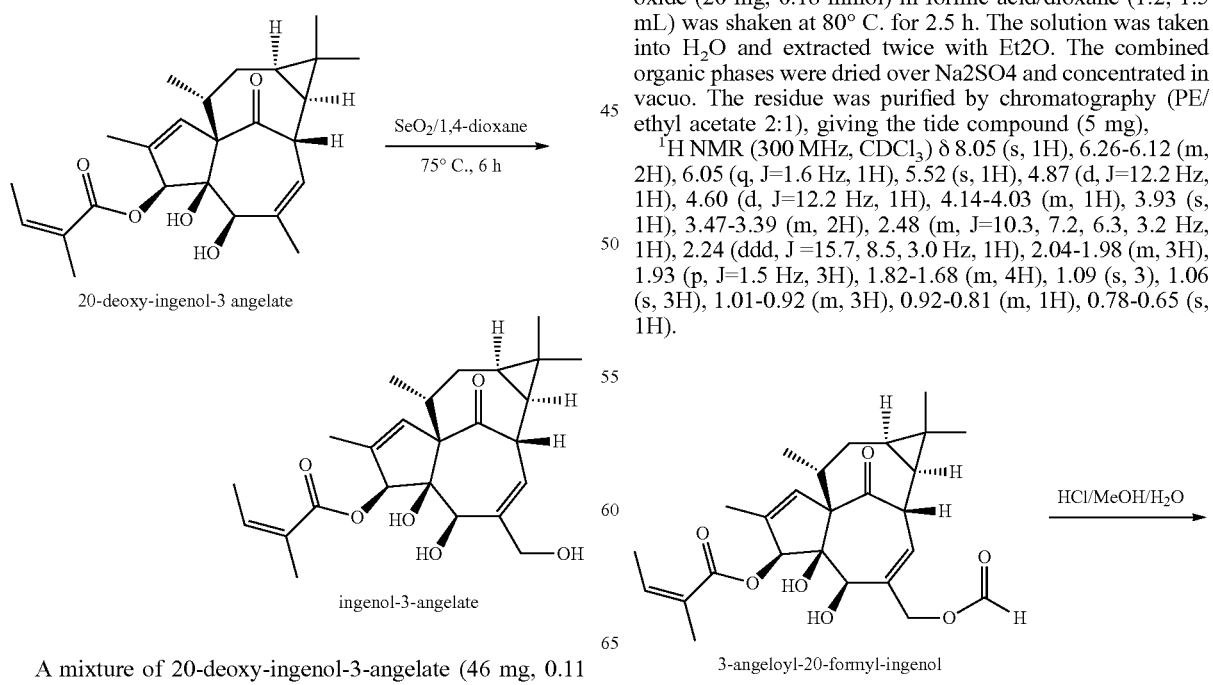

A mixture of 20-deoxy-ingenol-3-angelate (46 mg, 0.11 mmol) and SeO$_2$ (60 mg, 0.54 mmol) in 1,4-dioxane was heated to 80° C. in a closed reactor for 6 h. The mixture was filtered. The filtrate was concentrated in vacuo. The residue was purified by chromatography (petroleum ether/ethyl acetate 1:1), giving 19 mg of the desired product.

$^1$H NMR (300 MHz, CDCl$_3$) δ 6.16 (qq, J=7.2, 1.5 Hz, 1H), 6.10 -6.00 (m, 2H), 4.31 (d, J=4.4 Hz, 1H), 4.23-3.99 (m, 4H), 3.48 (s, 2H), 2.60-2.46 (m, 1H), 2.49-2.33 (m, 1H), 2.35-2.15 (m, 1H), 2.02 (dq, J=7.2, 1.7 Hz, 3H), 1.95-1.91 (m, 3H), 1.84-1.69 (m, 4H), 1.09 (s, 3H), 1.05 (s, 3H), 0.99-0.80 (m, 4H), 0.70 (td, J=8.5, 6.2 Hz, 1H).

Example 2

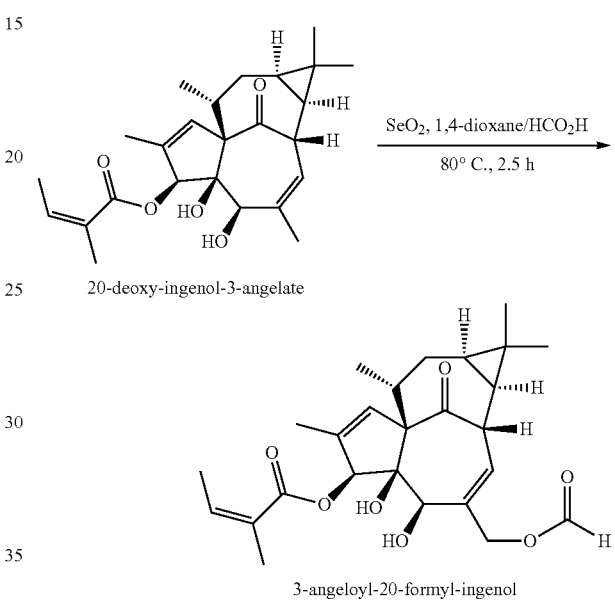

3-Angeloyl-20-Formyl-Ingenol

A solution of PEP006 (21 mg, 0.051 mmol), selenium oxide (20 mg, 0.18 mmol) in formic acid/dioxane (1:2, 1.5 mL) was shaken at 80° C. for 2.5 h. The solution was taken into H$_2$O and extracted twice with Et2O. The combined organic phases were dried over Na2SO4 and concentrated in vacuo. The residue was purified by chromatography (PE/ethyl acetate 2:1), giving the tide compound (5 mg), $^1$H NMR (300 MHz, CDCl$_3$) δ 8.05 (s, 1H), 6.26-6.12 (m, 2H), 6.05 (q, J=1.6 Hz, 1H), 5.52 (s, 1H), 4.87 (d, J=12.2 Hz, 1H), 4.60 (d, J=12.2 Hz, 1H), 4.14-4.03 (m, 1H), 3.93 (s, 1H), 3.47-3.39 (m, 2H), 2.48 (m, J=10.3, 7.2, 6.3, 3.2 Hz, 1H), 2.24 (ddd, J =15.7, 8.5, 3.0 Hz, 1H), 2.04-1.98 (m, 3H), 1.93 (p, J=1.5 Hz, 3H), 1.82-1.68 (m, 4H), 1.09 (s, 3), 1.06 (s, 3H), 1.01-0.92 (m, 3H), 0.92-0.81 (m, 1H), 0.78-0.65 (s, 1H).

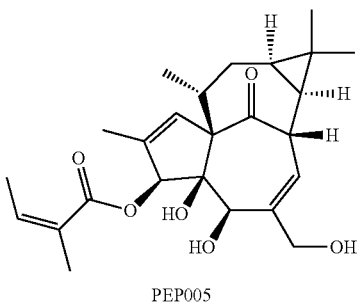

PEP005

PEP005

To a solution of 3-angeloyl-20-formyl-ingenol (5 mg, 0.011 mmol) in MeOH (0.5 mL) was added concentrated aqueous HO (0.025 mL) at rt. The solution was stirred at this temp for 0.5 h. The solution was concentrated in vacuo. The residue was purified by chromatography (petroleum ether/ethyl acetate 3:2 to 0:1), giving 4 mg of the product.

The invention claimed is:

1. A method for preparing ingenol-3-angelate, comprising:
reacting 20-deoxy-ingenol-3-angelate with an oxidizing agent to obtain ingenol-3-angelate.
2. The method of claim 1, wherein the oxidizing agent is selected from the group consisting of $SeO_2$, bis-(4-methoxyphenyl) selenoxide, $SiO_2$ and tert-butyl peroxide and mixtures thereof.
3. The method of claim 1, wherein said 20-deoxy-ingenol-3-angelate is obtained by conversion of 20-deoxy-ingenol using an activated angelic acid derivative.
4. The method of claim 2, wherein said oxidizing step is conducted with a solvent.
5. The method of claim 4, wherein said solvent is selected from the group consisting of 1,4 dioxane, formic acid/1,4 dioxane, methanol, acetic acid/dichloromethane, 1,2-dichloroethane and mixtures thereof.
6. The method of claim 5, wherein the oxidizing agent is $SeO_2$ and the solvent is 1,4 dioxane.
7. The method of claim 6, wherein the reacting step takes place at a temperature of at least 75° C.

* * * * *